United States Patent [19]
Brink

[11] Patent Number: 5,843,145
[45] Date of Patent: Dec. 1, 1998

[54] REUSABLE HOT/COLD TEMPERATURE PACK

[75] Inventor: N. Keith Brink, Oklahoma City, Okla.

[73] Assignee: Dura-Kold Corporation, Oklahoma City, Okla.

[21] Appl. No.: 590,141

[22] Filed: Jan. 23, 1996

[51] Int. Cl.$^6$ ...................................................... A61F 7/00
[52] U.S. Cl. ............................ 607/114; 607/96; 607/108; 607/112
[58] Field of Search ........................... 607/108–112, 114, 607/96, 104

[56] References Cited

U.S. PATENT DOCUMENTS 1,473,506  11/1923  Nessler .
1,567,931  12/1925  Epler .

(List continued on next page.)

FOREIGN PATENT DOCUMENTS 1185811  3/1970  United Kingdom .

OTHER PUBLICATIONS

Stockhausen, Inc. brochure entitled "FAVOR®–PAC Absorbent Polymers DATA—FAVOR® PAC Superabsorbent Polymers for Packaging Applications" (Mar. 1995).
Stockhausen, Inc. brochure entitled "The Absorber—News About Absorbent Polymers" (Jun. 1995) (pp. 7–8).
Photographs #1–#5.
Dura*Kold Corporation brochure entitled "Re–usable Ice Wrap".
Dura*Kold Corporation brochure entitled "Re–usable Compression Ice Wraps".
Dura*Kold Corporation brochure entitled "Equine, Re–usable Compression Ice Wraps".
Elasto–Gel brand Cervical Collar advertisement entitled "Elasto–Gel Cervical Collar provides soothing relief for all your pains in the neck!"; Elasto–Gel brand Sinus Mask advertisement entitled Say good–bye to those excruciating sinus–triggered migraines!.
ErgoMed Inc. advertisement entitled "Only ErgoForm™ contoured cold packs fit the treatment to the trauma".
Guardian Products Inc. brochure entitled "I.C.E. DOWN® A Refreezable Flexible Cold Therapy Wrap".
ICEWRAP™ brand advertisement entitled "Don't Miss Your Next Workout", from *Promises Kept* (Summer 1992).
QUINTA—Group Limited brochure entitled "MILD PACK™ Micro–Crystalline Ice For Long Duration".
Physicians & Nurses Manufacturing Corporation brochure entitled "COLD RELIEF Pack".
THERA•P brand brochure entitled "Say goodbye to melting ice and dripping towels!".
SPENCO® brand advertisement entitled "SPENCO® THERMAWRAP™ Compress".

(List continued on next page.)

*Primary Examiner*—John P. Lacyk
*Assistant Examiner*—Rosiland Kearney
*Attorney, Agent, or Firm*—McAfee & Taft

[57] ABSTRACT

A three component temperature pack, such as for use in a therapeutic hot/cold wrap applied to a human or animal, includes an outer casing, a gel contained within the casing, and one or more temperature cells contained within the casing with the gel. The gel provides heating or cooling after being charged by an external heating or cooling source, and yet it remains soft and flexible so that the pack is comfortable to a user. The one or more temperature cells provides heating or cooling to the gel even after the external heating or cooling source is removed, whereby the temperature pack provides prolonged heating or cooling. A method of manufacture provides for sequential controlled combining of three constituents of which a preferred gel is comprised, and it also provides for this in conjunction with filling and sealing the outer casing.

2 Claims, 1 Drawing Sheet

U.S. PATENT DOCUMENTS

| | | | |
|---|---|---|---|
| 1,927,751 | 9/1933 | Mensi . | |
| 1,964,962 | 7/1934 | Rosenblum . | |
| 2,547,886 | 4/1951 | Poux . | |
| 2,602,302 | 7/1952 | Poux . | |
| 2,769,308 | 11/1956 | Krasno . | |
| 2,800,456 | 7/1957 | Shepherd . | |
| 2,984,839 | 5/1961 | Conrad et al. . | |
| 3,149,943 | 9/1964 | Amador . | |
| 3,429,138 | 2/1969 | Goldmerstein . | |
| 3,463,161 | 8/1969 | Andrassy . | |
| 3,491,761 | 1/1970 | Baker . | |
| 3,500,014 | 3/1970 | Longo . | |
| 3,506,013 | 4/1970 | Zdenek . | |
| 3,802,215 | 4/1974 | Rowe . | |
| 3,871,376 | 3/1975 | Kozak . | |
| 3,889,684 | 6/1975 | Lebold . | |
| 3,900,035 | 8/1975 | Welch et al. . | |
| 3,913,559 | 10/1975 | Dandliker . | |
| 3,950,789 | 4/1976 | Konz et al. . | |
| 4,055,188 | 10/1977 | Pelton . | |
| 4,081,150 | 3/1978 | Tyson . | |
| 4,204,543 | 5/1980 | Henderson . | |
| 4,324,111 | 4/1982 | Edward . | |
| 4,326,533 | 4/1982 | Henderson . | |
| 4,341,649 | 7/1982 | Burns et al. . | |
| 4,377,075 | 3/1983 | Russo . | |
| 4,381,025 | 4/1983 | Schooley . | |
| 4,404,820 | 9/1983 | Romaine . | |
| 4,513,053 | 4/1985 | Chen et al. . | |
| 4,527,566 | 7/1985 | Abare . | |
| 4,556,055 | 12/1985 | Bonner, Jr. . | |
| 4,576,169 | 3/1986 | Williams . | |
| 4,619,678 | 10/1986 | Rubin . | |
| 4,625,729 | 12/1986 | Roney . | |
| 4,628,932 | 12/1986 | Tampa . | |
| 4,676,247 | 6/1987 | Van Cleve . | |
| 4,688,572 | 8/1987 | Hubbard et al. . | |
| 4,700,706 | 10/1987 | Münch . | |
| 4,708,812 | 11/1987 | Hatfield . | |
| 4,832,030 | 5/1989 | De Casto . | |
| 4,832,031 | 5/1989 | Last . | |
| 4,865,012 | 9/1989 | Kelley . | |
| 4,887,590 | 12/1989 | Logue et al. . | |
| 4,931,333 | 6/1990 | Henry . | |
| 4,938,207 | 7/1990 | Vargo . | |
| 4,941,462 | 7/1990 | Lindberg . | |
| 4,962,761 | 10/1990 | Golden | 607/104 |
| 4,981,135 | 1/1991 | Hardy | 607/108 |
| 5,005,374 | 4/1991 | Spitler | 62/259.3 |
| 5,069,208 | 12/1991 | Noppel et al. | 607/114 |
| 5,353,975 | 10/1994 | Libertucci | 224/224 |
| 5,385,688 | 1/1995 | Miller et al. | 252/73 |
| 5,391,198 | 2/1995 | Cheney, III et al. | 607/114 |
| 5,395,399 | 3/1995 | Rosenwald | 107/108 |
| 5,415,624 | 5/1995 | Williams | 602/21 |
| 5,443,488 | 8/1995 | Namenye et al. | 607/104 |
| 5,462,517 | 10/1995 | Mann | 602/26 |
| 5,484,448 | 1/1996 | Steele et al. | 607/108 |
| 5,496,358 | 3/1996 | Rosenwald | 607/108 |
| 5,507,793 | 4/1996 | Hodges | 607/109 |

OTHER PUBLICATIONS

SmartPractice advertisement entitled "ThermoCare™ The All–In–One Hot And Cold Pack".

EBI® Medical Systems advertisement entitled "EBI® Temptek™ vs. Ice: Compare the Cold, Hard Facts", from *Orthopaedic Review*.

Breg™ brochure entitled "Polar Care™ Cold Therapy".

CRYO/CUFF™ brand brochure entitled "CRYO/CUFF™ compression dressings".

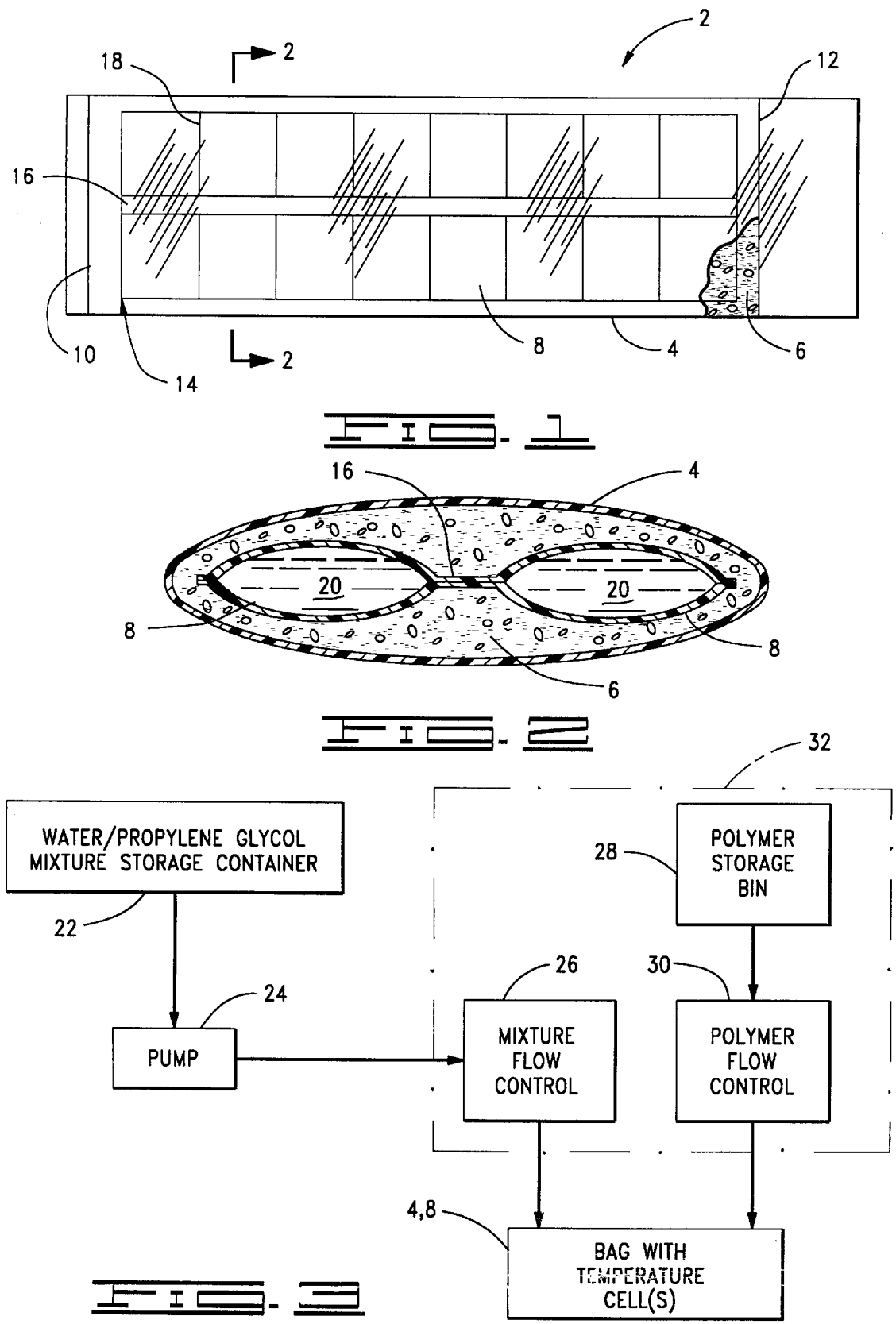

REUSABLE HOT/COLD TEMPERATURE PACK

BACKGROUND OF THE INVENTION

This invention relates generally to temperature packs and methods of manufacturing them. It relates more particularly, but not by way of limitation, to such temperature packs for use in hot/cold therapy wraps applied to body portions of humans and animals.

The efficacy of hot and cold therapy for humans and animals is well known. Devices used for this range from ice bags and hot water bottles to wraps through which temperature treated water flows.

One type of such a device with which the present invention can be used, but to which the invention is not limited, is a hot/cold therapeutic wrap that has at least one compartment into which a temperature pack is placed. The temperature pack is the mechanism that retains a heated or cooled state in response to the application of an external heating or cooling source and thereafter dissipates the heat or cold when the therapeutic wrap containing the pack is put in use.

One example of a temperature pack is the type used in prior therapeutic wraps from Dura-Kold Corporation, the assignee of the present invention. This type of pack comprises a single temperature responsive substance contained in a plastic "bubble" type mat (i.e., a mat of integrally connected "bubbles" or cells containing a temperature responsive liquid). Another type of temperature pack has a clay based temperature responsive substance.

The present invention focuses on the temperature pack and not the overall wrap, whereby the utility of the present invention is not necessarily limited to therapeutic wraps. With regard to just the temperature pack, prior types that use a single type of temperature responsive substance have at least one of the following two shortcomings: discomfort and/or limited therapeutic (heat/cold retention) time. As to the former shortcoming, a temperature pack having a temperature responsive substance that becomes solid at its in-use temperature is uncomfortable when secured to the body portion to be treated. As to the latter shortcoming, the therapeutic time is limited to how long the single temperature responsive substance retains a therapeutic temperature.

In view of at least these two shortcomings, there is the need for an improved temperature pack, such as for use in a therapeutic wrap, that preferably is both comfortable and longer-lasting when heated or cooled to a desired temperature.

SUMMARY OF THE INVENTION

The present invention overcomes the above-noted and other shortcomings of the prior art by providing a novel and improved temperature pack. The present invention also provides a method of manufacturing such a device.

The temperature pack remains relatively soft and flexible even when cooled, whereby it is comfortable to someone who wears the pack for cold therapy. The temperature pack also preferably has a prolonged heating or cooling period once it has been charged by an external heating or cooling source.

The temperature pack of the present invention having both of the aforementioned advantages comprises a flexible outer casing and a gel contained inside the outer casing. The gel is responsive to heating or cooling the temperature pack so that the gel becomes heated or cooled but remains in a gel state whereby the gel provides cushioning to the temperature pack even when the gel is heated or cooled. This temperature pack further comprises a temperature cell contained inside the outer casing with the gel. The temperature cell has a fluid filled chamber wherein the fluid is also responsive to the heating or cooling of the temperature pack so that the fluid becomes heated or cooled for maintaining the gel in a prolonged heated or cooled condition in response to the heating or cooling of the temperature pack.

With regard to at least the comfort advantage, the present invention can be defined as a temperature pack comprising casing means for conforming to a portion of a human or animal body to which heat or cold therapy is to be applied. This temperature pack further comprises a gel contained inside the casing means. The gel is responsive to heat or cold applied to the temperature pack so that the gel becomes heated or cooled but remains in a gel state for providing cushioning means to the temperature pack for cushioning the portion of a human or animal body to which the temperature pack is applied even when the gel is heated or cooled. The gel specifically includes a composition of water, propylene glycol and a superabsorbent polymer.

The method of the present invention comprises combining water and propylene glycol into a mixture; storing the mixture in a storage container; inserting a closed temperature cell into a leak-resistant bag defining an outer casing of the temperature pack; moving a controlled amount of the mixture from the storage container into the bag containing the temperature cell; moving a controlled amount of a superabsorbent polymer into the bag in contact with the controlled amount of mixture pumped into the bag; and sealing the bag to retain the temperature cell, the controlled amount of mixture and the controlled amount of superabsorbent polymer therein.

Therefore, from the foregoing, it is a general object of the present invention to provide a novel and improved temperature pack and a method of manufacturing the same. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is a plan view of the preferred embodiment temperature pack of the present invention.

FIG. 2 is a sectional view taken along line 2—2 shown in FIG. 1.

FIG. 3 is a block diagram of a system used for implementing the method of the present invention.

DETAILED DESCRIPTION OF PREFERRED EMBODIMENTS

The preferred embodiment of a temperature pack 2 according to the present invention will be described with reference to FIGS. 1 and 2. A related method of manufacture will then be described with reference to FIG. 3.

FIGS. 1 and 2 show that the temperature pack 2 comprises a flexible outer casing 4 which contains both (1) a gel-like substance simply referred to herein as a gel 6 and (2) one or more temperature cells 8.

The outer casing 4 of the preferred embodiment provides a means for conforming to a portion of a human or animal body to which heat or cold therapy is to be applied. As such a means, it is contemplated that the temperature pack 2 will be inserted into an outer jacket such as of the type used in prior hot/cold therapy wraps from Dura-Kold Corporation of Oklahoma City, Okla.

In a particular implementation, the outer casing 4 includes a polyethylene and ethylene-vinyl acetate copolymer (EVA) bag. A specific implementation includes a minimum 0.0055 mil polyethylene plastic bag with a minimum of 4% EVA. The EVA is preferably used to enhance the following bag characteristics: strength, heat diffusion, watertightness, and suitability for both heat and cold applications.

The outer casing 4 can have any suitable size. For applications such as human or animal therapy, bag widths of 3 inches, 5 inches and 10 inches with a length of 12 inches are non-limiting examples.

The outer casing 4 is made such that it has one closed end such as indicated by seal line 10 in FIG. 1. This end and the surrounding side of the casing 4 define an internal cavity or compartment in which the gel 6 and the temperature cell(s) 8 are disposed. Once the gel 6 and the cell(s) 8 have been placed in the compartment of the casing 4, the previously open end is sealed as indicated by seal line 12 in FIG. 1.

The gel 6 contained inside the outer casing 4 is responsive to external heating or cooling that is applied to the temperature pack 2. For example, the pack 2 can be heated in a microwave oven in one or more intervals of about twenty seconds each until a desired temperature is reached. Another example is to heat the pack 2 in a pan of hot tap water for from three to five minutes. As to cooling, the pack 2 can be left in a conventional residential freezer until ready for use, for example.

Despite being heated or cooled such as explained above, the gel remains in a gel-like state whereby it provides cushioning means to the temperature pack even when heated or cooled. This cushioning is for the benefit of the portion of a human or animal body to which the temperature pack 2 is applied in the aforementioned application of hot or cold therapy.

In the preferred embodiment, the gel is a composition including water, propylene glycol and a superabsorbent polymer. The composition preferably consists essentially of only these three constituents.

The water can be of any suitable type. The values given hereinbelow are with regard to tap water, but other water can be used (e.g., purified, distilled, or de-ionized). The type of water used will likely affect the ratios of the other constituents.

The propylene glycol provides the flexibility that facilitates the cushioning effect of the gel even when cooled. The propylene glycol is preferably of commercial grade; one supplier of this is Harcros Chemicals Inc. of Kansas City, Kans. Propylene glycol is the term used herein to refer to the substance having synonyms which include 1,2 propanediol; propanediol-1,2; and 1,2-dihydroxypropane.

In a particular implementation, the superabsorbent polymer is a crosslinked homopolymer of partially neutralized acrylic acid. One particular product that provides this is FAVOR® PAC 210 from Stockhausen, Inc. of Greensboro, N.C. This is a crosslinked homopolymer of partially neutralized acrylic acid, some versions of which may contain a polyalcohol. Neutralization is accomplished with a sodium hydroxide solution. In its dry form, this particular product is a granular powder of crystalline structure. Upon swelling with water, it yields a gel-like suspension. The uptake of water is facilitated by the negative carboxylic groups of the polymer and their hydration with water molecules. The negative carboxylic groups give this brand of polymers a high negative surface charge. Due to its crosslinking, this brand of polymer is essentially insoluble in water. However, incomplete crosslinking results in small amounts of "water extracts" that can be leached out of the polymer matrix by water. High salt concentrations lead to reduced swelling capacity during gel formation and hence to smaller amounts of water extracts. Bivalent and trivalent cations can quickly exchange the sodium and bind themselves to the polymer via the negative carboxylic groups. This leads to shrinkage of the gel, which then becomes inert.

Another supplier of a suitable superabsorbent polymer is Nalco Chemical Company of Naperville, Ill.

In a particular implementation of the present invention, the water and propylene glycol are mixed in a ratio of about 13:3 by volume of water to propylene glycol. This mixture is then combined with the superabsorbent polymer in the ratio of about 192:1 by volume of mixture to polymer. This 192:1 ratio specifically applies to the aforementioned brand of crosslinked homopolymer of partially neutralized acrylic acid.

The one or more temperature cells 8 also respond to the applied heat or cold whereby this temperature element becomes heated or cooled. This element then heats or cools the gel after the externally applied heat or cold is removed from the overall temperature pack 2. This provides means for heating or cooling the gel after the external heat or cold is no longer applied to the temperature pack so that heating or cooling provided by the gel is prolonged. Accordingly, the present invention provides for prolonged continuous hot or cold therapy to the portion of the human or animal body to which the temperature pack is applied (in at least one application of the present invention).

In the preferred embodiment, the temperature cell element is implemented by a temperature mat 14, such as the type previously used in conventional hot/cold therapy wraps provided by Dura-Kold Corporation. One specific source for this is Cryopak Corporation of Port Roberts, Wash.

The mat 14 has a plurality of the cells 8 integrally connected along connecting webs 16, 18 whereby each cell is in a respective fixed position relative to the other cells as illustrated in FIGS. 1 and 2, thereby forming a "bubble-pack" configuration. Each of the "bubbles" or cells 8 has a flexible plastic body containing a liquid 20 which substantially freezes to a solid state when cooled to a suitable temperature (e.g., 30° F.) for use in providing cold therapy to a human or animal. The mat 14 can also preferably be heated to a heat treatment temperature (e.g., 150°–180° F.) so that the pack 2 can alternatively be used for heat therapy. In either instance (i.e., cooled or heated), the temperature-responsive liquid 20 of each cell 8 provides its cold or heat for prolonging the cooled or heated state of the gel 6.

A preferred method of manufacturing the aforementioned temperature pack 2 will be described next with reference to FIG. 3.

The water and propylene glycol are combined into a mixture and stored in a mixture storage container 22. This preferably provides a sufficient batch of mixture to produce a plurality of the temperature packs 2. The container 22 is preferably sealed to prevent evaporation of the mixture. In a particular implementation, the water and propylene glycol are manually poured together into a fifteen gallon container.

The method also includes inserting a closed temperature cell, such as the cells 8 of the temperature mat 14, into the leak-resistant bag defined by the outer casing 4. With the temperature mat 14 inside the outer casing 4, each cell 8 of the mat 14 not only is fixed relative to each other cell 8 as mentioned above but also is substantially fixed relative to the outer casing 4 as apparent from the small surrounding clearances in FIGS. 1 and 2. That is, as shown in FIGS. 1 and 2 in this embodiment of the present invention the temperature mat 14 can shift slightly left or right and up or down in view of the small surrounding clearances, but the cells 8 are otherwise limited to their respective positions.

A controlled amount of the mixture is then moved from the storage container 22 into the bag 4 containing the temperature cell(s) 8. This occurs in the illustrated method by pumping, such as with a pump 24 (e.g., a 20 psi Granger pump), through a mixture flow control device 26 which controls the amount of mixture pumped into the bag 4.

Concurrently with moving a controlled amount of the mixture into the bag 4, a controlled amount of the superabsorbent polymer is moved into the bag in contact with the controlled amount of mixture. This occurs in a particular implementation by metering the dry polymer from a storage bin 28 through a polymer flow control device 30 into the bag 4.

A particular implementation of the mixture flow control device 26, the polymer storage bin 28 and the polymer flow control device 30 is provided by a control apparatus 32, such as a "Gel-Master" machine from Norman Campbell of Estacada, Oreg. This has a controllable valve implementing the mixture flow control device 26 and a metering auger implementing the polymer flow control device 30.

Once the controlled amounts of mixture and polymer are flowed into the bag 4 containing the one or more temperature cells 8 (such as implemented by the mat 14), the bag 4 is sealed to retain the contents therein. This can be implemented such as with a ³⁄₁₆ inch automatic bar sealer from American Electric Inc.

The mixture flow control device 26 and the polymer flow control device 30 operate in a particular implementation to produce a ratio between the mixture and the superabsorbent polymer of about 192:1 by volume of mixture to polymer. As previously mentioned, the mixture of this particular implementation is preferably in the ratio of about 13:3 by volume of water to propylene glycol. The metering by the devices 26, 30 occurs automatically once timing control is set by suitably adjusting controls on the "Gel-Master" machine used in the aforementioned particular implementation.

The following examples are illustrative and not limiting of the present invention.

EXAMPLE 1

A mixture of twenty-six fluid ounces of tap water and six fluid ounces of propylene glycol was manually formed by pouring the amounts together. Then eight fluid ounces of this mixture was poured into a five-inch by twelve-inch plastic bag and one-fourth teaspoon of FAVOR® PAC 210 superabsorbent polymer was added to form a gel in accordance with one embodiment of the present invention. This bag with the gel was then placed in a freezer at 0° F. for two hours. At the end of the two hours, the bag and its contents were removed from the freezer and left exposed at room temperature (72° F.). After one hour the mixture had thawed and the bag had an external temperature of 34° F.

EXAMPLE 2

An ice mat containing a two by eight array of cells from Cryopak Corp. was placed in the same freezer used in Example 1 at 0° F. for two hours. The ice mat was then removed from the freezer and left exposed at room temperature (72° F.). After one hour the contents of the ice mat had thawed and the ice mat had an external temperature of 46° F.

EXAMPLE 3

The ice mat (the one used in Example 2) was placed inside the plastic bag (the one used in Example 1) with a gel including eight fluid ounces of the mixture and one-fourth teaspoon of the superabsorbent polymer as formed in Example 1 to form a pack of the present invention. This pack was then placed in the same freezer used in Example 1 at 0F for two hours. After the two hours, this pack was removed from the freezer and left exposed at room temperature (72° F.). The thaw time for the gel was one hour, thirty-seven minutes but the ice mat was still frozen. The total thaw time was two hours, four minutes at which time the external bag temperature was 39° F.

The foregoing Examples 1 and 2 show that the gel of the present invention provided prolonged cooling relative to the ice mat when each was tested separately. Example 3 shows that the overall pack of the present invention provided significantly longer cooling than the individual gel and ice mat alone.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A temperature pack, comprising:

a flexible outer casing;

a gel contained inside said outer casing, said gel responsive both to heating and cooling externally applied to said temperature pack so that said gel becomes heated or cooled depending on whether heating or cooling is applied to said temperature pack and remains in a heated or cooled state during a prolonged continuous hot or cold therapy period after the externally applied heating or cooling is removed but remains in a gel state whereby said gel provides cushioning to said temperature pack even when said gel is heated or cooled; and a temperature cell contained inside outer casing and disposed in said gel, said temperature cell having a fluid filled chamber wherein the fluid is also responsive both to the heating and cooling externally applied to said temperature pack so that said fluid becomes heated or cooled and remains in a heated or cooled state during the prolonged continuous hot or cold therapy period after the externally applied heating or cooling is removed such that at least the prolonged continuous cold therapy period is at least about two hours.

2. A temperature pack, comprising:

casing means for conforming to a portion of a human or animal body to which heat or cold therapy is to be applied; and a gel contained inside said casing means, said gel responsive to heat or cold applied to said temperature pack so that said gel becomes heated or cooled but remains in a gel state for providing cushioning means to said temperature pack for cushioning the portion of a human or animal body to which said temperature pack is applied even when said gel is heated or cooled, said gel including a composition of water, propylene glycol and a superabsorbent polymer, wherein the water and propylene glycol are mixed in a ratio of about 13:3 by volume of water to propylene glycol and this mixture is combined with the superabsorbent polymer in the ratio of about 192:1 by volume of mixture to polymer.

\* \* \* \* \*

UNITED STATES PATENT AND TRADEMARK OFFICE
CERTIFICATE OF CORRECTION

PATENT NO. : 5,843,145

DATED : December 1, 1998

INVENTOR(S) : N. Keith Brink

It is certified that error appears in the above-identified patent and that said Letters Patent is hereby corrected as shown below:

Column 6, line 4, change "OF" to --0° F--.

column 6, lines 27-48 (claim 1), with the following:

--1. A temperature pack, comprising:

a flexible outer casing;

a gel contained inside said outer casing, said gel responsive to heating or cooling said temperature pack so that said gel becomes heated or cooled but remains in a gel state whereby said gel provides cushioning to said temperature pack even when said gel is heated or cooled, wherein said gel is a composition consisting essentially of water, propylene glycol and a superabsorbent polymer and said superabsorbent polymer is a crosslinked homopolymer of partially

UNITED STATES PATENT AND TRADEMARK OFFICE
CERTIFICATE OF CORRECTION

PATENT NO. : 5,843,145
DATED : December 1, 1998
INVENTOR(S) : N. Keith Brink

It is certified that error appears in the above-identified patent and that said Letters Patent is hereby corrected as shown below:

>    neutralized acrylic acid and further
>    wherein the water and propylene glycol
>    are mixed in a ratio of about 13:3 by
>    volume of water to propylene glycol and
>    this mixture is combined with the
>    crosslinked homopolymer of partially
>    neutralized acrylic acid in the ratio of
>    about 192:1 by volume of mixture to
>    crosslinked homopolymer; and
>
> a temperature cell contained inside said outer
>    casing with said gel, said temperature
>    cell having a fluid filled chamber
>    wherein the fluid is also responsive to
>    the heating or cooling of said
>    temperature pack so that said fluid
>    becomes heated or cooled for maintaining
>    said gel in a prolonged heated or cooled
>    condition in response to the heating or
>    cooling of said temperature pack.--

Signed and Sealed this

Twenty-seventh Day of April, 1999

Attest:

Q. TODD DICKINSON

*Attesting Officer*       *Acting Commissioner of Patents and Trademarks*